United States Patent [19]

Enhsen et al.

[11] Patent Number: 5,466,815
[45] Date of Patent: Nov. 14, 1995

[54] TETRAZOLE DERIVATIVES OF BILE ACIDS, AND THEIR USE AS LIPID LEVEL LOWERING MEDICAMENTS

[75] Inventors: Alfons Enhsen, Büttelborn; Heiner Glombik, Hofheim; Werner Kramer, Mainz; Günther Wess, Erlensee, all of Germany

[73] Assignee: Hoechst Aktiengesellschaft, Frankfurt am Main, Germany

[21] Appl. No.: 238,741

[22] Filed: May 5, 1994

[30]     Foreign Application Priority Data

May 8, 1993 [DE] Germany .................... 43 15 368.2

[51] Int. Cl.⁶ .................... C07D 257/06; A61K 31/41
[52] U.S. Cl. .................... 548/252; 548/253; 548/112
[58] Field of Search .................... 548/252, 251; 514/381, 382

[56]             References Cited

U.S. PATENT DOCUMENTS 5,250,524  10/1993  Kramer et al. .................... 514/177

FOREIGN PATENT DOCUMENTS

0489423A1  6/1992  European Pat. Off. .

OTHER PUBLICATIONS

"Synthesis of 24–nor–5β–cholan–23–oic acid derivatives: a convenient and efficient one–carbon degradation of the side chain of natural bile acids", Schteingart et al., Journal of Lipid Research, 29:1387–1395 (1988).

"Synthesis of Mosesin–4, a Naturally Occurring Steroid Saponin with Shark Repellent Activity, and Its Analog 7-β-Galactosyl Ethyl Cholate", Gargiulo et al., *Tetrahedron*, 45(17):5423–5432 (1989).

"Angiotensin II receptor binding inhibitors", Hodges et al., Drugs of the Future, 17(7):575–593 (1992).

*Primary Examiner*—David B. Springer
*Attorney, Agent, or Firm*—Finnegan, Henderson, Farabow, Garrett & Dunner

[57]             ABSTRACT

The invention relates to tetrazole derivatives of bile acids, processes for their preparation, and use of these compounds as medicaments and cholesterol lowering agents. The tetrazole-bile acid derivatives are of the formula G1—X—G2, where G1 is H, a bile acid radical, or a bile acid radical which is modified on the hydroxyl functions and/or on the carboxyl group, X is a single bond or a bridge group between G1 and G2, and G2 is of the formula:

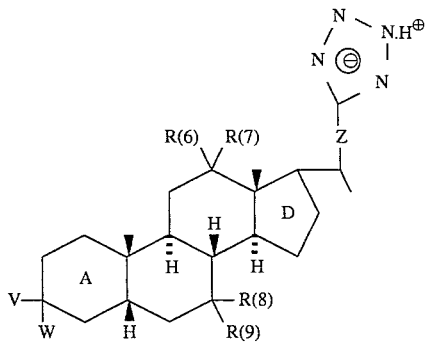

8 Claims, No Drawings

5,466,815

TETRAZOLE DERIVATIVES OF BILE ACIDS, AND THEIR USE AS LIPID LEVEL LOWERING MEDICAMENTS

DESCRIPTION

The invention relates to bile acid derivatives of the formula I

G1—X—G2 processes for their preparation, pharmaceutical preparations based on these compounds and the use of the bile acid derivatives as medicaments.

The compounds according to the invention have a high affinity for the specific bile acid transportation system of the small intestine and inhibit bile acid resorption in a concentration-dependent and competitive manner.

Bile acids have an important physiological function in lipolysis, for example as cofactors of pancreatic lipases and as natural detergents for solubilization of fats and fat-soluble vitamins. As the end product of cholesterol metabolism, they are synthesized in the liver, stored in the gallbladder and secreted from this by contraction into the small intestine, where they display their physiological action. The greatest proportion of bile acids secreted is recovered via the enterohepatic circulation. They return to the liver by the mesenterial veins of the small intestine and the portal vein system. Both active and passive transportation processes play a role in re-absorption in the intestine. A large proportion of the bile acids is reabsorbed at the end of the small intestine, the terminal ileum, by a specific $Na^+$-dependent transportation system and return to the liver with the mesenterial venous blood via the portal vein, to be secreted again by the liver cells into the bile. Bile acids occur in the enterohepatic circulation both as free acids and in the form of glycine conjugates and taurine conjugates.

Non-absorbable, insoluble, basic, crosslinked polymers have been used for a long time for binding bile acids, and have been used therapeutically on the basis of these properties. Bile acid derivatives described in patent application EP-A-0 489 423 have a high affinity for the intestinal bile acid transportation system and therefore allow specific inhibition of the enterohepatic circulation. All diseases where inhibition of bile acid resorption in the intestine, in particular in the small intestine, seems desirable are regarded as therapeutic subjects. For example, biligenic diarrhea following ileum resection, or increased blood cholesterol levels are treated in this manner. In the case of an increased blood cholesterol level, a reduction in this level can be achieved by intervention in the enterohepatic circulation. Reducing the bile acid pool in the enterohepatic circulation forces corresponding new synthesis of bile acids from cholesterol in the liver. The LDL cholesterol in the blood circulation is resorted to in order to meet the cholesterol requirement in the liver, the hepatic LDL receptors being increasingly used. The acceleration in LDL catabolism achieved in this way has the effect of reducing the atherogenic cholesterol content in the blood.

Most natural bile acids have a terminal carboxyl group (carbon atom 24) in the side chain on the D ring of the steroid structure. The carboxyl group is in the free form or is conjugated with an amino acid.

The tetrazol-5-yl group is an isosteric group to the carboxyl function, i.e. it has similar steric, electronic and acid properties to the carboxyl function itself. It is known from medical chemistry that when the carboxyl group of certain active compounds is replaced by a tetrazol-5-yl radical, the affinity for enzymes and proteins is retained or increased and a better action potential can thus be achieved (Drugs of the Future 1992, 17 (7) 575 to 593).

The object was to discover novel medicaments which are capable of reducing the atherogenic cholesterol content in the blood or of influencing the enterohepatic circulation in respect of increased secretion of bile acid and subsequent reduction in the cholesterol level.

This object is achieved by the tetrazole-bile acid derivatives according to the invention.

The invention therefore relates to tetrazole-bile acid derivatives of the formula I

G1—X—G2        I in which

G1 is H, a bile acid radical or a modified bile acid radical which is modified on the hydroxyl functions and/or on the carboxyl group and G2 is a bile acid radical or a bile acid radical derivatized on the hydroxyl functions, which carries a tetrazolyl radical in the side chain, and X is a bridge group or a covalent bond, and in which G1 and G2 can be bonded via X as desired.

The compounds according to the invention have a high affinity for the specific bile acid transportation system of the small intestine and inhibit bile acid resorption in a concentration-dependent and competitive manner.

Furthermore, the compounds according to the invention are not themselves absorbed and therefore do not enter into the blood circulation. The enterohepatic circulation of bile acid can be interrupted very specifically and efficiently by application of this action principle.

By using the compounds according to the invention it is possible to reduce the amount of bile acid in the enterohepatic circulation, so that a reduction in the cholesterol level in the serum takes place. Avitaminoses are just as unlikely during use as an influence on the absorption of other medicaments or an adverse effect on the intestinal flora. The side-effects known to be caused by polymers (constipation, steatorrhea) furthermore are not observed, i.e. lipolysis is not adversely influenced. Because of the high affinity for the specific bile acid transportation system of the small intestine, low daily doses are sufficient, so that acceptance of such medicaments by the doctor and patient will be very high.

Preferred compounds of the formula I are those in which the linkage between the steroid structures of G1 and G2 is not via in each case the same rings of the steroid structure, and in which X is a covalent bond or a bridge group, G1 is H, a bile acid radical or a bile acid radical modified on the hydroxyl functions and/or on the carboxyl group and G2 is a bile acid radical or a bile acid radical derivatized on the hydroxyl functions, which carries a tetrazolyl radical in the side chain.

Particularly preferred compounds of the formula I are those in which the linkage of G1 and G2 is via the ring D of G1 and the ring A of G2, and in which G1 is H or a radical of the formula II,

Formula II (steroid structure with R(2), R(3), R(1)O, R(4), R(5) substituents and side chain ending in CHO)

in which

R(1) is H, an alkyl radical or alkenyl radical having up to 10 carbon atoms, which is branched or unbranched, a cycloalkyl radical having 3 to 8 carbon atoms, a benzyl radical, which is unsubstituted or mono- to trisubstituted by F, Cl, Br, $(C_1-C_4)$-alkyl or $(C_1-C_4)$-alkoxy, a diphenylmethyl radical, which is unsubstituted or mono- to trisubstituted by F, Cl, Br, $(C_1-C_4)$-alkyl or $(C_1-C_4)$-alkoxy, a triphenylmethyl radical, which is unsubstituted or mono- to trisubstituted by F, Cl, Br, $(C_1-C_4)$-alkyl or $(C_1-C_4)$-alkoxy, a $C_1-C_4$-alkoxymethyl or a tetrahydroxylamyl radical, or a radical $$O=\overset{OL}{\underset{OL}{P}}-,\quad O=\overset{OL}{\underset{O}{S}}-\quad\text{or}\quad L-\overset{O}{\underset{}{C}}-$$

in which L is H, an alkyl or alkenyl radical having up to 10 carbon atoms, which is branched or unbranched, a cycloalkyl radical having 3 to 8 carbon atoms, a phenyl radical, which is unsubstituted or mono- to trisubstituted by F, Cl, Br, $(C_1-C_4)$-alkyl or $(C_1-C_4)$-alkoxy, or a benzyl radical, which is unsubstituted or mono- to trisubstituted by F, Cl, Br, $(C_1-C_4)$-alkyl or $(C_1-C_4)$-alkoxy, X is a single bond or a bridge member of the formula III $$-[-(N)_s-A-\underset{L(1)}{N}-\overset{O}{\underset{L(2)}{C}}-(CH_2)_q-\overset{O}{C}-]_r-\underset{L(3)}{N}-(B)_t-$$

in which

A is an alkylene chain, which is branched or unbranched and can optionally be interrupted by —O—, —S— or phenylene, the linkage to the phenylene ring being in the ortho-, meta- or para-position and the chain comprising in total 2 to 12, preferably 2 to 6, chain members p, B is an alkylene chain, which is branched or unbranched and can optionally be interrupted by —O—, —S— or phenylene, the linkage to the phenylene ring being in the ortho-, meta- or para-position and the chain comprising in total 2 to 12, preferably 2 to 6, chain members n, L(1), L(2) and L(3) are identical or different and have the meaning of L, and q is 0 to 5 r is 0 or 1, s is 0 or 1 and t is 0 or 1,

R(2) to R(5), where R(2) and R(3) or R(4) and R(5) in each case together are the oxygen of a carbonyl group, or individually and in each case independently of one another are H, —OL, —SL, —NHL, tetrahydropyranyloxy or $C_1-C_4$-alkoxymethoxy, in which n has the abovementioned meaning, and G2 is a radical of the formula IV (steroid structure with R(6), R(7), R(8), R(9), V, W substituents and tetrazole-containing side chain with Z linker)

in which Z is $$-(CH_2)_m-\left(\overset{O}{\underset{H}{\underset{|}{N}}}\right)_n-(CH_2)_o-$$

where m is zero to 4, n is zero or 1 and o is zero to 4

V —O—, $-\underset{L}{N}-$, —CH$_2$—, —CH$_2$CH$_2$—

W is H or, if V is —CH$_2$ or —CH$_2$CH$_2$—, is also OH and R(6) to R(9) have the meaning given under R(2) to R(5).

Especially preferred compounds of the formula I are those in which G1 is H or a radical of the formula II (steroid structure with R(2), R(3), R(1)O, R(4), R(5) substituents and side chain ending in CHO)

in which

R(1) is H, formyl, acetyl, benzoyl, methoxymethyl or tetrahydropyranyl,

R(2) to R(5), where R(2) and R(3) or R(4) and R(5) in each case together are the oxygen of a carbonyl group, or individually and independently of one another are H, OH, O-formyl, O-acetyl, O-benzoyl, methoxymethoxy or tetrahydropyranyloxy, X is a covalent bond or one of the following bridge groups

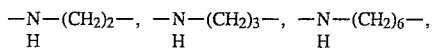

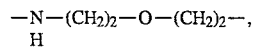

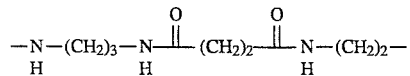

G2 is a radical of the formula IV

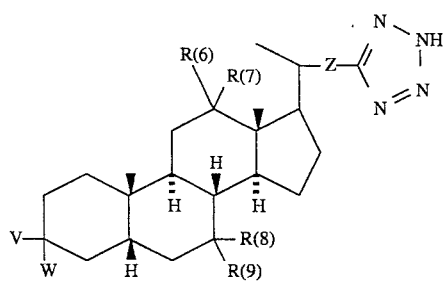

in which
V is —O—,

W is H,

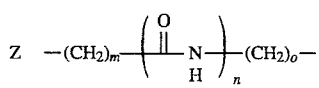

where m is 1 to 3, n is zero or 1 and o is zero, 1 or 2, and

R (6) to R(9) have the meaning given above under R(2) to R(5).

The invention furthermore relates to a process for the preparation of compounds of the formula I, which comprises a) in the case where X=a single bond, reacting suitable reactive forms of G1 and G2 with one another by processes which are known in principle, or b) in the case where X=a bridge group, reacting
   α) reactive forms of G1-X with G2 or
   β) reactive forms of G2-X with G1
with one another by processes which are known in principle.

a) X=a single bond

The bile acids G1 are employed either in the free form or in protected form. After linkage with G2, which is likewise in the free or protected form, the protective groups are split off, if appropriate. Suitable protective groups for the alcohol groups are expediently formyl, acetyl or tetrahydropyranyl. The tetrazolyl function is either already present in G2 before the linking operation, or is introduced via a carboxyl group of G2 after the linking with G1.

For example, bile acid preferentially reacts at position 3, but also at position 7, with activated forms of carboxylic acids, such as acid chlorides or mixed anhydrides, with addition of bases, such as trialkylamine or pyridine, or also NaOH, at room temperature in suitable solvents, such as tetrahydrofuran, methylene chloride or ethyl acetate, or else dimethylformamide (DMF) or dimethoxyethane (DME). The various isomers can be separated, for example, by chromatography. The reaction can be carried out selectively by using suitable protective groups.

Corresponding amino-bile acids can be converted into corresponding amides analogously. Here also, the reaction can be carried out either with protected or with free bile acids.

Other compounds according to the invention can be linked analogously by known standard processes.

b) X=a bridge member

The processes described under a) are also used to carry out the linking of G1-X with G2 or G1 with X-G2.

Here also, the bile acid portion is expediently employed in either protected or unprotected form. A preferred preparation process comprises reacting reactive forms of G1 with reactive forms of X-G2. If appropriate, the linking operation is followed by splitting off protective groups and converting into a tetrazole derivative.

The preparation of tetrazolyl-bile acid units or tetrazolyl-bile acids is described in the following equations.

Equation 1

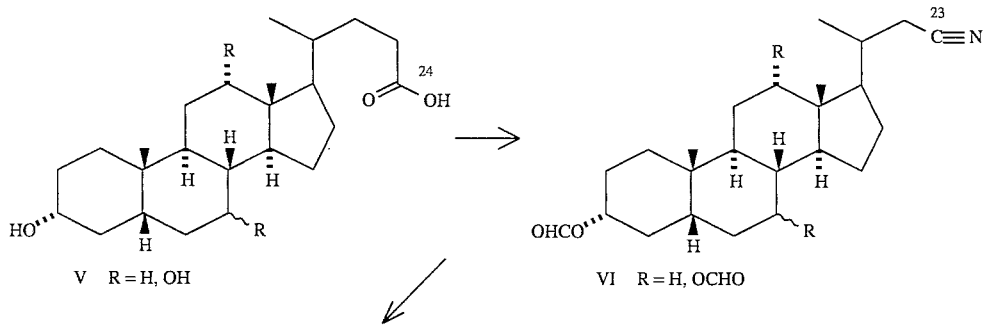

-continued
Equation 1

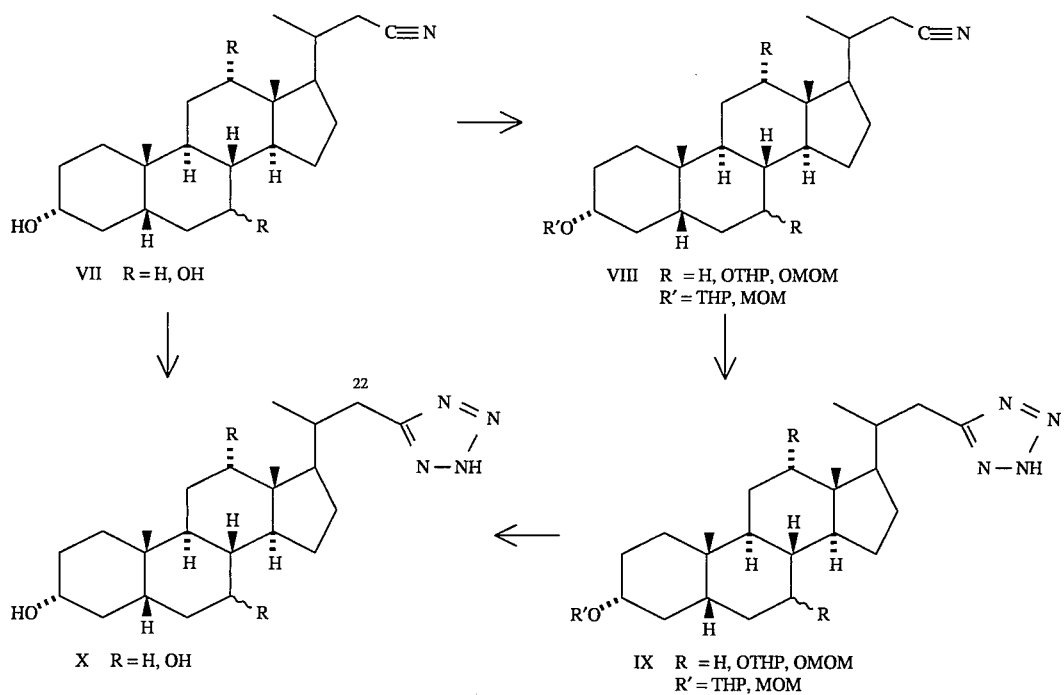

VII  R = H, OH

VIII  R = H, OTHP, OMOM
R' = THP, MOM

X  R = H, OH

IX  R = H, OTHP, OMOM
R' = THP, MOM

THP = tetrahydropyranyl, MOM = methoxymethyl

C-22-tetrazolyl-cholanic acid derivatives X are accessible by first shortening the side chain of a C-24-cholanic acid V by one carbon atom to give the nitrile VI (J. Lip. Res. 29, 1387, 1988). The protective groups are split off by hydrolysis under mild conditions, and compounds of the type VII are obtained. These nitriles VII can then be reacted directly with trialkyl-tin azides in a suitable solvent, such as, for example, toluene, at elevated temperatures to give the tetrazole derivatives X. However, it may be advantageous to protect the free OH groups, for example with THP or MOM protective groups to give the compounds VIII, before the tetrazole formations. The reaction to give the protected tetrazole derivative IX is carried out under the conditions described above. Splitting off the protective groups again leads to compounds of the type X.

Equation 2

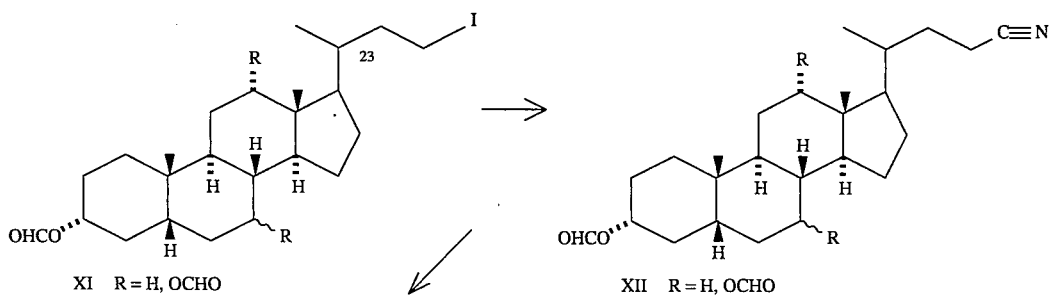

XI  R = H, OCHO

XII  R = H, OCHO

-continued
Equation 2

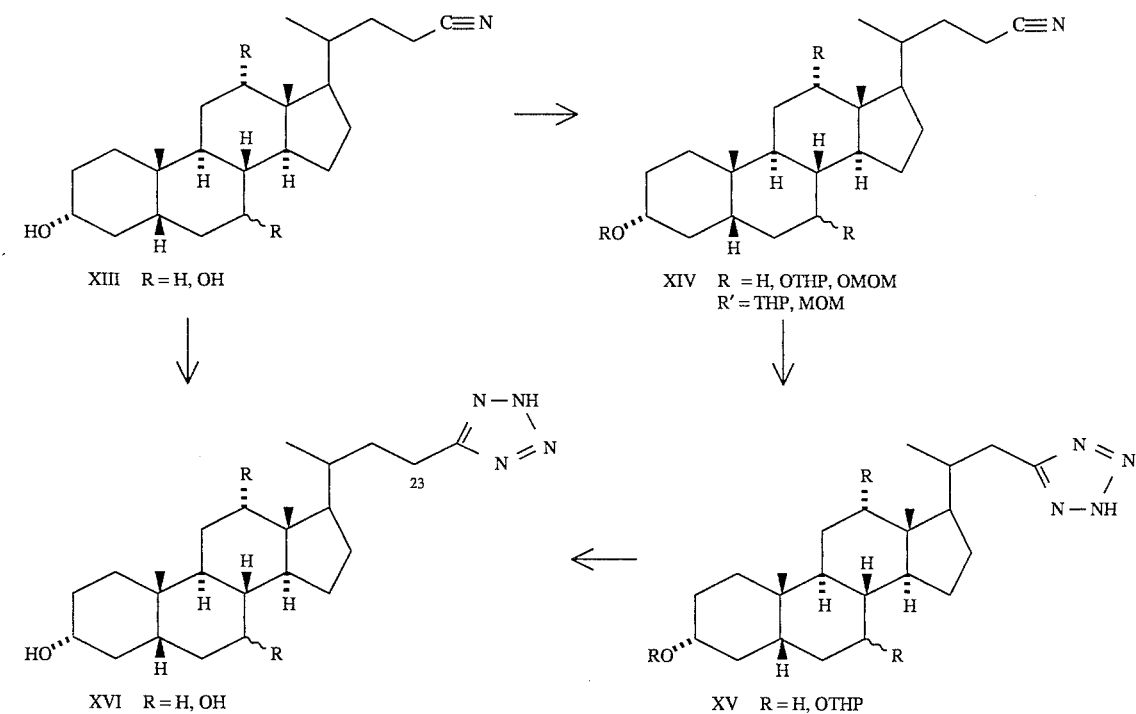

To prepare C-23-tetrazolylcholanic acids XVI, for example, iodine compounds of the type XI are converted into nitriles XII by nucleophilic substitution with alkali metal cyanides. After the protective groups have been split off, the nitriles XIII can either be reacted directly to give the tetrazole compounds XVI, or the possible route via protected derivatives XIV and XV can also be utilized.

Equation 3

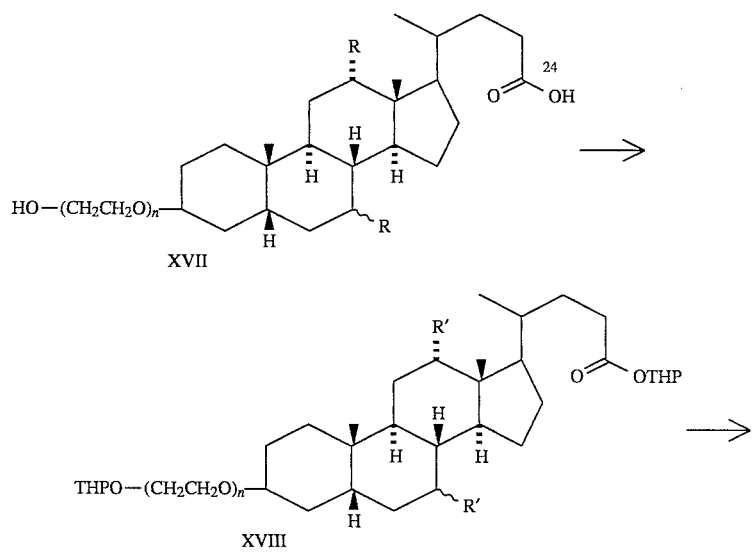

Equation 3
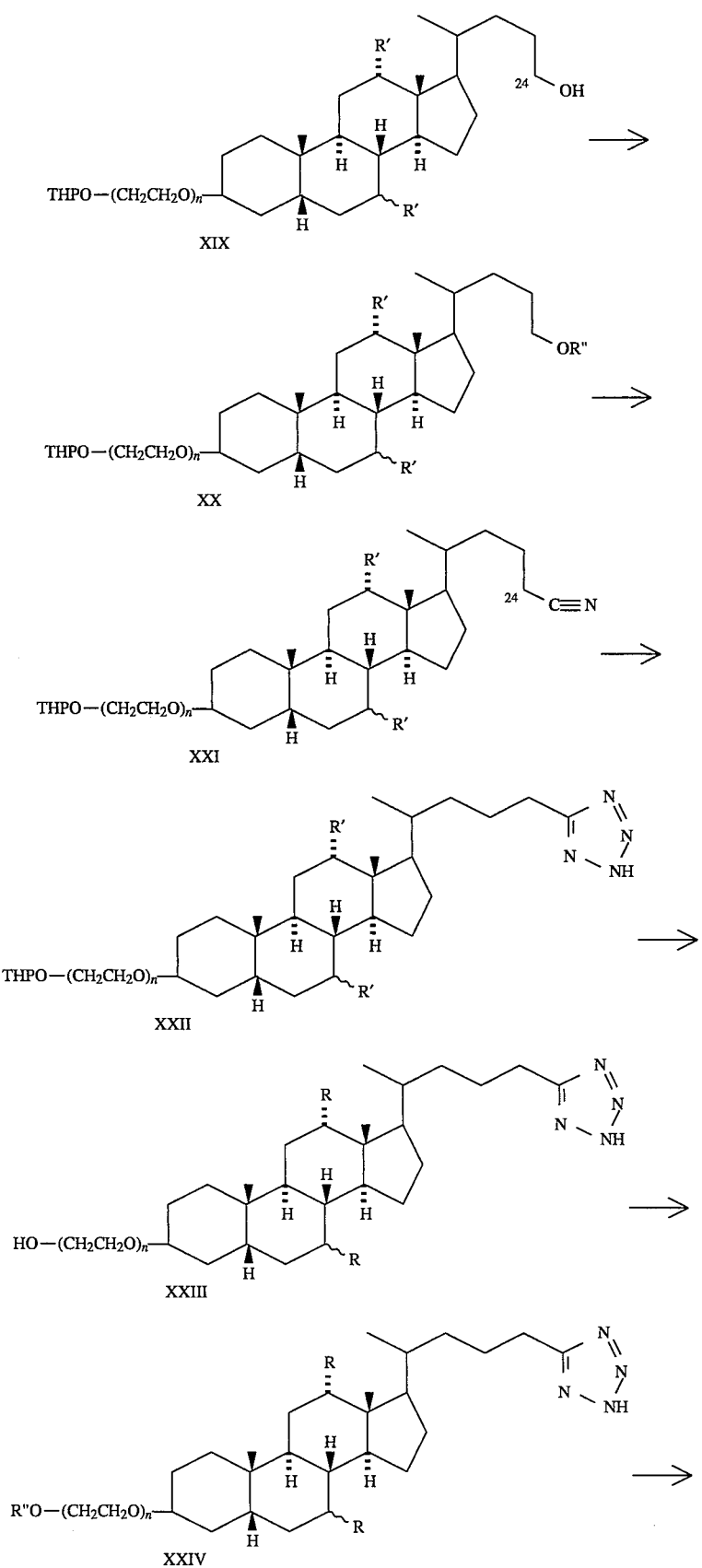

Equation 3

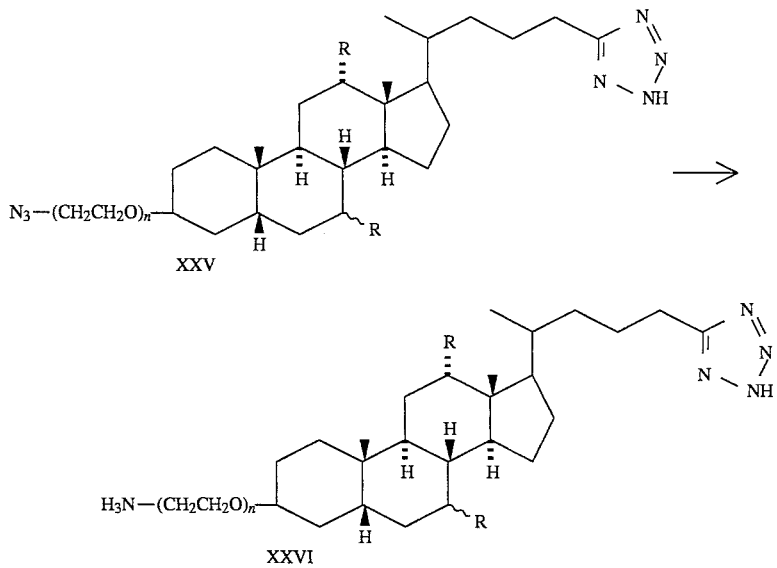

R = H, OH; R' = H, OTHP; R" = mesyl, tosyl; n = 0, 1, 2

C-24-tetrazole derivatives are obtained by providing compounds of the type XVII with protective groups on the hydroxyl groups and on the acid function. The resulting ester functions of compounds of the type XVIII are reduced to primary hydroxyl groups (XIX). The hydroxyl group is activated by a methane- or toluenesulfonyl radical (XX), and subjected to substitution with an alkali metal cyanide; this gives compounds of the type XXI. The reaction of nitrile to give tetrazolyl compounds (XXII) and the subsequent splitting-off of the protective groups to give XXIII are carried out by the processes described above. From the free hydroxyl function in position 3 or in the bonding member X introduced, an amino function can be prepared via compounds of the formulae XXIV and XXV analogously to processes already described (EP-A-O 489 423), and compounds of the type XXVI are obtained.

Equation 4

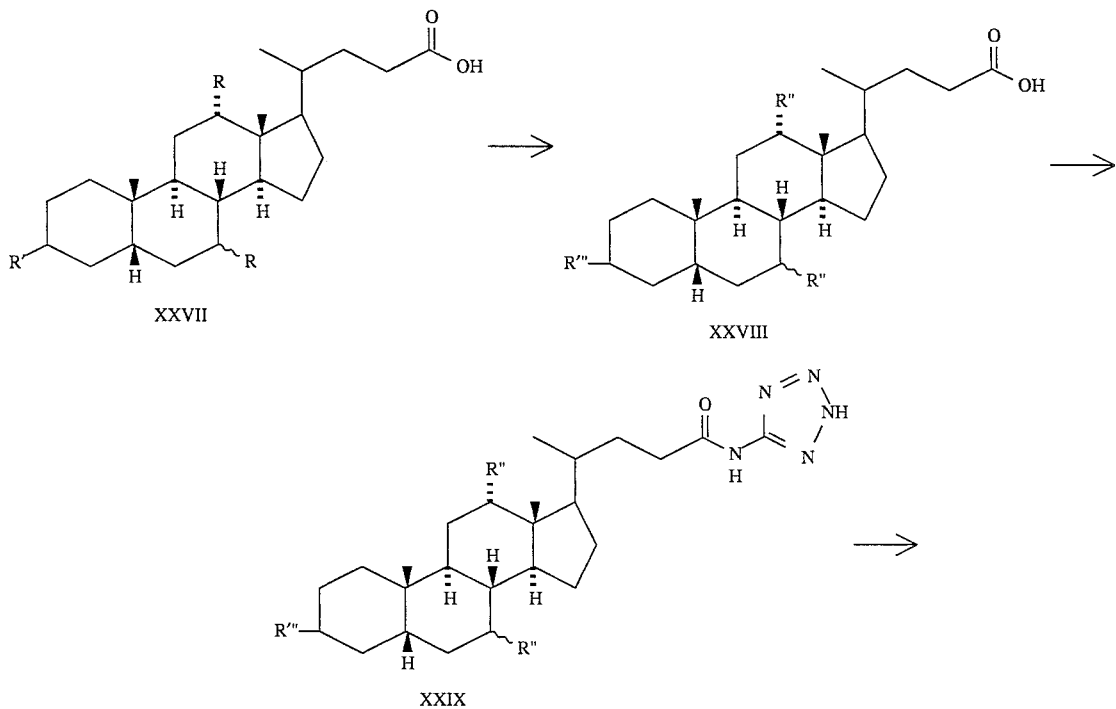

-continued
Equation 4

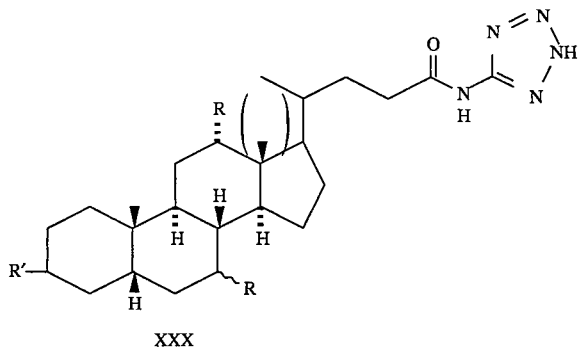
XXX

R= H, OH
R' = OH or

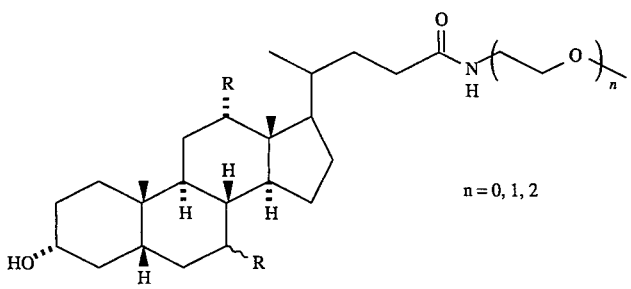
n = 0, 1, 2

R"= H, OCHO, OCOCH₃
R'" = OCHO, OCOCH₃ or

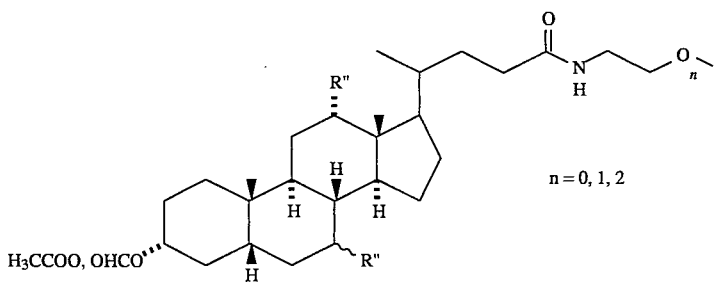
n = 0, 1, 2

Tetrazole derivatives can be prepared from natural bile acids or also from modified bile acids, for example from dimeric derivatives, by reacting the free carboxyl group with 5-aminotetrazole, after activation. If the usual peptide coupling reagents are used, the yields of this reaction are low. It is therefore expedient to protect the free hydroxyl functions of the bile acid derivative XXVII, for example with formyl or acetyl protective groups. The acid chloride is produced from the protected compounds XXVIII with phosphorus pentachloride or thionyl chloride, for example in THF. Reaction of the acid chloride with dry 5-aminotetrazole gives compounds of the type XXVIX, from which the end products XXX can be obtained by simply splitting off the protective groups.

The compounds have useful pharmacological properties and are therefore particularly suitable as hypolipidemic agents.

The invention also relates to medicaments based on the compounds of the formula (I) and to the use of the compounds as medicaments, in particular for lowering the cholesterol level.

The compounds according to the invention were tested biologically by determination of the inhibition of [$^3$H]-taurocholate uptake in brush border membrane vesicles of the ileum of rabbits. The inhibition test was carried out as follows:

1. Preparation of Brush Border Membrane Vesicles from the Ileum of Rabbits

Brush border membrane vesicles were prepared from the intestinal cells of the small intestine by the so-called $Mg^{2+}$ precipitation method. Male New Zealand rabbits (2 to 2.5 kg bodyweight) were sacrificed by intravenous injection of 0.5 ml of an aqueous solution of 2.5 mg Tetracain HCl, 100 T61$^R$ and 25 mg of mebezonium iodide. The small intestine was rinsed with ice-cold physiological saline solution. The terminal 7/10 of the small intestine (measured in the oral-rectal direction, i.e. the terminal ileum, which contains the active Na$^+$-dependent bile acid transportation system) was used for preparation of the brush border membrane vesicles. The intestines were frozen in plastic bags under nitrogen at −80° C. For preparation of the membrane vesicles, the frozen intestines were cooled at 30° C. in a water-bath. The mucosa was scraped off and suspended in 60 ml of ice-cold 12 mM Tris/HCl buffer (pH 7.1)/300 mM mannitol, 5 mM EGTA/10 mg/l of phenylmethylsulfonylfluoride/1 mg/l of trypsin inhibitor for soya beans (32 U/mg)/0.5 mg/l of trypsin inhibitor from bovine lung (193 U/mg)/5 mg/l of bacitracin. After dilution to 300 ml with ice-cold distilled water, the mixture was homogenized with an Ultraturrax (18-rod, IKA Werk Staufen, FRG) for 3 minutes at 75 % of the maximum power, while cooling with ice. After addition of 3 ml of 1M MgCl$_2$ solution (final concentration 10 mM), the mixture was left to stand at 0° C. for exactly 1 minute. By addition of Mg$^{2+}$, the cell membranes aggregate and precipitate, with the exception of the brush border membranes. After centrifugation at 3000×g (5000 revolutions per minute, SS-34 rotor) for 15 minutes, the precipitate is discarded and the supernatant, which contains the brush border membranes, was centrifuged at 267000×g (15000 revolutions per minute, SS-34 rotor) for 30 minutes. The supernatant was discarded and the precipitate was rehomogenized in 60 ml of 12 mM tris/HCl buffer (pH 7.1)/60 mM mannitol, 5 mM EGTA using a Potter Elvejhem homogenizer (Braun, Melsungen, 900 revolutions per minute, 10 strokes). After addition of 0.1 ml of 1M MgCl$_2$ solution and an incubation time of 15 minutes at 0° C., the mixture was centrifuged again at 3000×g for 15 minutes. The supernatatant was then centrifuged again at 46000×g (15000 revolutions per minute, SS-34 rotor) for 30 minutes. The precipitate was taken up in 30 ml of 10 mM Tris/Hepes buffer (pH 7.4)/300 mM mannitol and resuspended homogeneously by 20 strokes in a Potter Elvejhem homogenizer at 1000 revolutions per minute. After centrifugation at 48000×g (20000 revolutions per minute, SS-34 rotor) for 30 minutes, the precipitate was taken up in 0.5 to 2 ml of Tris/Hepes buffer (pH 7.4)/280 mM mannitol (final concentration 20 mg/ml) and resuspended with the aid of a tuberculin syringe with a 27 gauge needle. The vesicles were either used for transportation studies immediately after preparation or stored at −196° C. in 4 mg portions in liquid nitrogen.

2. Inhibition of the Na$^+$-dependent [$^3$H]-taurocholate Uptake in the Brush Border Membrane Vesicles of the Ileum The uptake of substrates into the brush border membrane vesicles described above was determined by means of the so-called membrane filtration technique. 10 μl of the vesicle suspension (100 μg of protein) were pipetted as drops onto the wall of a polystyrene incubation tube (11×70 mm) which contained the incubation medium with the corresponding ligands (90 μl). The incubation medium contained 0.75 μl=0.75 μCi of [$^3$H(G)]-taurocholate (specific activity: 2.1 Ci/mMol)/0.5 μl of 10 mM taurocholate/8.75 μl of sodium transportation buffer (10 mM Tris/Hepes (pH 7.4)/100 mM mannitol/100 mM NaCl) (Na-T-B) or 8.75 μl of potassium transportation buffer (10 ml Tris/Hepes (pH 7.4)/100 mM mannitol/100 mM KCl) (K-T-B) and 80 μl of the inhibitor solution in question, dissolved in Na-T buffer or K-T buffer, depending on the experiment. The incubation medium was filtered through a polyvinylidene fluoride membrane filter (SYHV LO 4NS, 0.45 μm, 4 mm ⌀, Millipore, Eschborn, FRG). The transportation measurement was started by mixing the vesicles with the incubation medium. The concentration of taurocholate in the incubation batch was 50 μM. After the desired incubation time (usually 1 minute), the transportation was stopped by addition of 1 ml of ice-cold stopping solution (10 mM Tris/Hepes (pH 7.4)/150 mM KCl). The resulting mixture was filtered with suction over a membrane filter of cellulose nitrate (ME 25, 0.45 μm, 25 mm diameter, Schleicher & Schuell, Dassell, FRG) under a vacuum of 25 to 35 mbar. The filter was rinsed with 5 ml of ice-cold stopping solution.

To measure the uptake of the radioactively labeled taurocholate, the membrane filter was dissolved with 4 ml of the scintillator Quickscint 361 (Zinsser Analytic GmbH, Frankfurt, FRG) and the radioactivity was measured by liquid scintillation measurement in a Tri-Carb 2500 measuring instrument (Canberra Packard GmbH, Frankfurt, FRG). After calibration of the apparatus with the aid of standard samples and after correction for any chemiluminescence present, the values measured were obtained as dpm (decompositions per minute).

The control values were determined in each case in Na-T-B and K-T-B. The difference between the uptake in Na-T-B and K-T-B gave the Na$^+$-dependent transportation content. That concentration of inhibitor at which the Na$^+$-dependent transportation content was inhibited by 50%—based on the control—was designated the IC$_{50}$Na$^+$.

The pharmacological data comprise a test series in which the interaction of the compounds according to the invention with the intestinal bile acid transportation system in the terminal small intestine was investigated. The results are summarized in Table 1.

The invention furthermore relates to the use of the compounds according to the invention for the preparation of a medicine.

For this, the compounds of the formula I are dissolved or suspended in pharmacologically acceptable organic solvents, such as mono- or polyhydrate alcohols, such as, for example ethanol or glycerol, or in triacetin, oils, for example sunflower oil or cod-liver oil, ethers, such as, for example, diethylene glycol dimethylether, or else polyethers, for example polyethylene glycol, or also in the presence of other pharmacologically acceptable polymeric carriers, such as, for example, polyvinylpyrrolidone, or other pharmaceutically acceptable additives, such as starch, cyclodextrin or polysaccharides. The compounds according to the invention furthermore can be administered in combination with the other medicaments.

The compounds of the formula I are administered in various dosage forms, preferably orally in the form of tablets, capsules or liquids. The daily dose varies in the range from 3 mg to 5000 mg, but preferably in the dose range from 10 to 1000 mg, depending on the body weight and constitution of the patient.

EXAMPLE 1

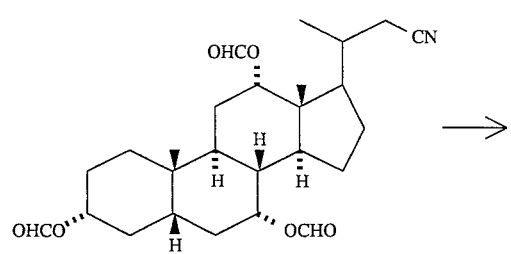

-continued

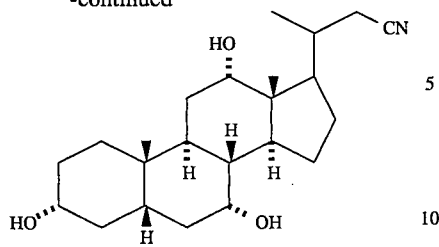

The protective groups were removed from 5.0 g (10.9 mmol) of the triformyl compound (J. Lip. Res. 29, 1387, 1988) in 100 ml of 1M NaOMe/MeOH solution at room temperature for 2 hours. For working up, water is added and the methanol is stripped off. The mixture is extracted three times with $CH_2Cl_2$, dried over $MgSO_4$ and concentrated. 3.9 g (96%) of the unprotected nitrile are obtained.

MS (FAB, 3-NBA/LiCl) $C_{33}H_{37}NO_3$ (375) 383 (M+Li$^+$)

EXAMPLE 2

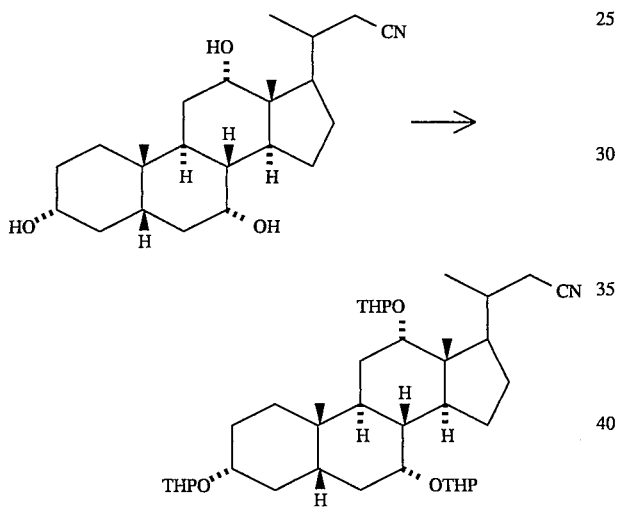

3.8 g (10.1 mmol) of trihydroxy compound (Example 1) are dissolved in 40 ml of $CH_2Cl_2$, 20 ml of dihydropyran and 300 mg of pyridinium 4-toluenesulfonate are added at 0° C. and the reaction mixture is then stirred at room temperature for 2 days. It is concentrated and the residue is chromatographed over silica gel (cyclohexane/ethyl acetate 2:1). 5.7 g (90%) of product are obtained.

MS (FAB, 3-NBA/LiCl) $C_{33}H_{53}NO_5$ 8543) 550 (M+Li$^+$)

EXAMPLE 3

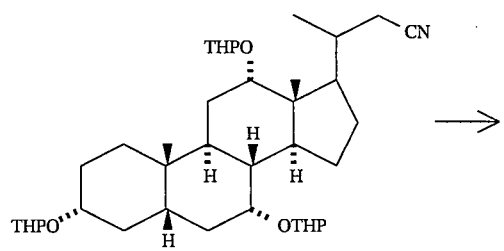

-continued 2.0 g (3.19 mmol) of nitrile (Example 2) and 2.1 g (6.34 mmol) of tributyl-tin azide are heated under reflux in toluene for 6 days. After 3 days, a further 2.1 g of tributyl-tin azide are added. The reaction mixture is concentrated. After chromatography of the residue (silica gel, ethyl acetate/MeOH 95:5), 1.7 g (79%) of tetrazole derivative are obtained.

MS (FAB, 3-NBA/LiCl) $C_{38}H_{62}N_4O_6$ (670) 677 (M+Li$^+$)

EXAMPLE 4

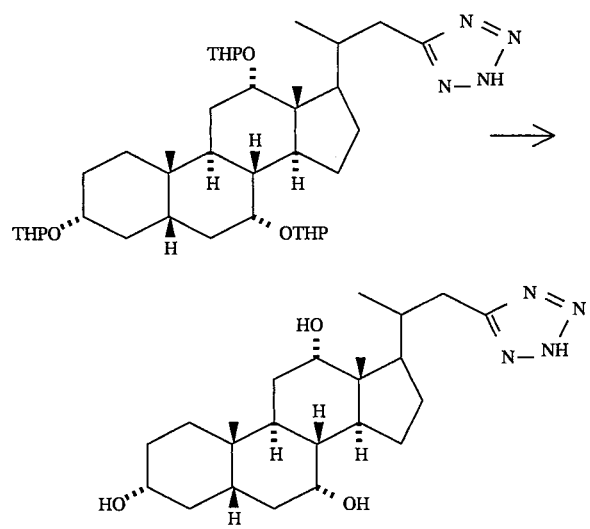

1.6 g (2.39 mmol) of THP-protected compound (Example 3), 200 mg of pyridinium p-toluenesulfonate and 1.6 ml of acetic acid are heated under reflux in 30 ml of methanol for 12 hours. After cooling, the mixture is concentrated and the residue is chromatographed over silica gel ($CH_2Cl_2$/MeOH 9:1). Yield: 720 mg (87%)

MS (FAB, 3-NBA/LiCl) $C_{23}H_{38}N_4O_3$ (418) 425 (M+Li$^+$)

EXAMPLE 5

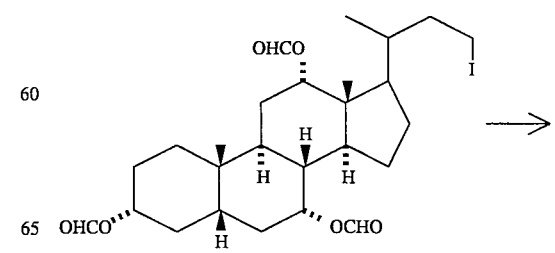

-continued

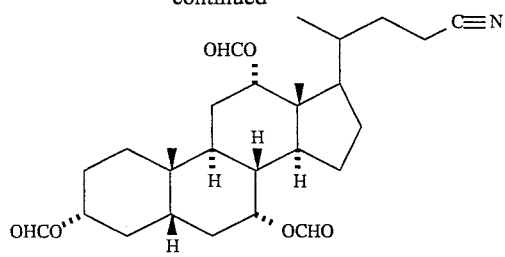

21 g (36.6 mmol) of iodine compound (Tetrahedron, 45 (17), 5423, 1989) and 3.6 g of sodium cyanide are stirred in 300 ml of DMSO at 50° C. for 1.5 hours. The reaction mixture is poured onto ice-water and extracted with ethyl acetate. The organic phase is dried (MgSO$_4$) and concentrated. Chromatography (cyclohexane/ethyl acetate) gives 15 g (87%) of nitrile.

MS (FAB, 3-NBA/LiCl) C$_{27}$H$_{39}$NO$_6$ (473) 480 (M+Li$^+$)

EXAMPLE 6

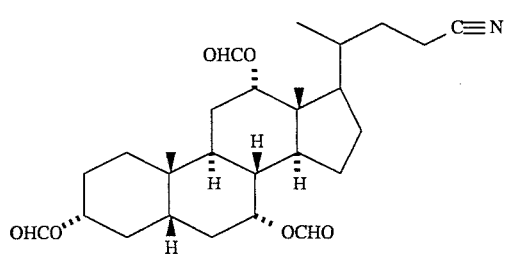 

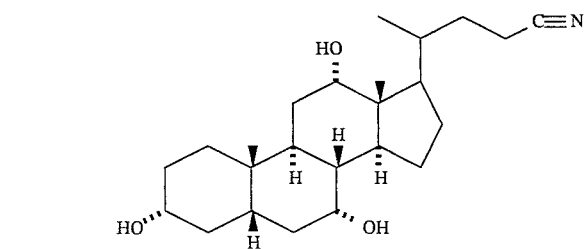

The protective groups are removed from the compound protected by formyl (Example 5) by the process described for Example 1.

MS (FAB, 3-NBA/LiCl) C$_{24}$H$_{39}$NO$_3$ (389) 396 (M+Li$^+$)

Examples 7, 8 and 9 were prepared by the process described for Examples 2, 3 and 4.

EXAMPLE 7

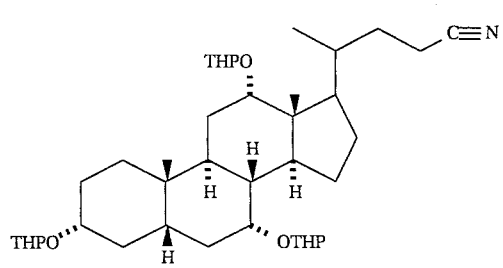

MS (FAB, 3-NBA/LiCl) C$_{39}$H$_{63}$NO$_6$ (641) 648 (M+Li$^+$)

EXAMPLE 8

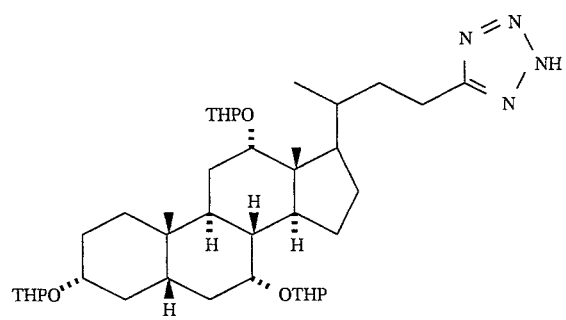

MS (FAB, 3-NBA/LiCl) C$_{39}$H$_{64}$N$_4$O$_6$ (684.5) 691.6 (M+Li$^+$)

EXAMPLE 9

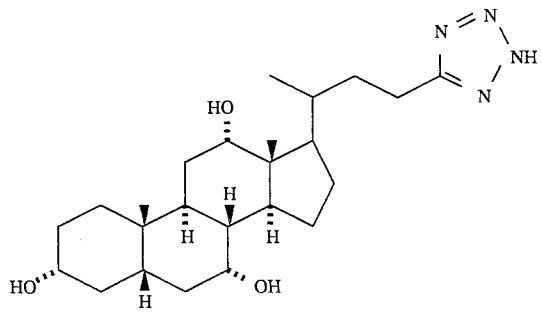

MS (FAB, 3-NBA/LiCl) C$_{24}$H$_{40}$N$_4$O$_3$ (432) 439 (M+Li$^+$)

The compound of Example 9 can also be obtained directly from Example 6 and tributyl-tin azide (see Example 3). The crude product is chromatographed twice for purification (1. ethyl acetate/MeOH 9:1; 2. CH$_2$Cl$_2$/MeOH/acetic acid 9:1:0.1). The yield is 83%.

EXAMPLE 10

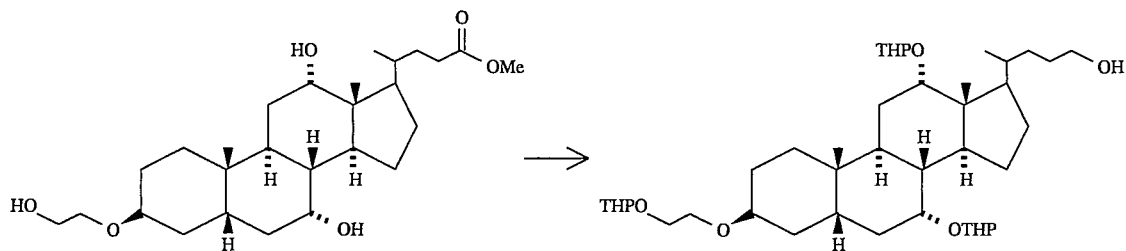

100 g (215 mmol) of trihydroxy compound (EP-A-0 489 423) are protected with tetrahydropyranyl groups according to Example 2. The resulting crude product is reacted without further purification. As a solution in 250 ml of ether, it is slowly added dropwise to a suspension of 15 g of LiAlH$_4$ in 500 ml of ether at 0° C. After 2 hours at 0° to 5° C., water is carefully added and the mixture is then extracted several times with ether. The organic phase is dried (MgSO$_4$) and concentrated. 100 g (67%) of product are obtained.

EXAMPLE 11

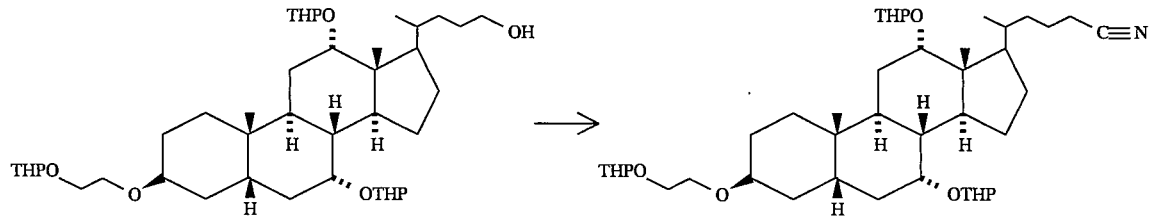

20 g (29.0 mmol) of the alcohol (Example 10) are dissolved in 150 ml of pyridine. 2.45 ml (31.0 mmol) of methanesulfonyl chloride are slowly added dropwise at 0° C. and the mixture is then stirred at room temperature for 2 hours. For working up, the mixture is poured onto ice-water and extracted with ethyl acetate. The organic phase is dried (MgSO$_4$) and concentrated. The crude product is dissolved in 200 ml of DMSO, 3.0 g of NaCN are added and the mixture is stirred at 50° C. for 1 hour. It is poured onto ice-water and extracted with ethyl acetate. After the organic phase has been dried, the residue is concentrated and chromatographed (cyclohexane/ethyl acetate 7:3). 15 g (77%) of nitrile are obtained.

MS (FAB, 3-NBA/LiCl) C$_{42}$H$_{69}$NO$_7$ (699) 706 (M+Li$^+$)

EXAMPLE 12

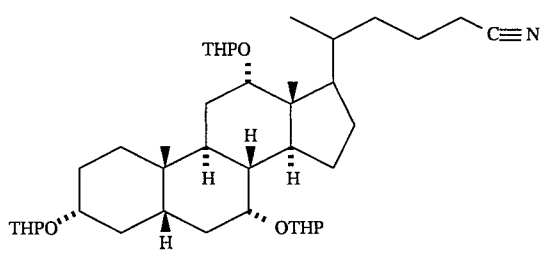

Example 12 was obtained by the process described for Example 11.

Examples 13 to 16 are prepared by the processes described for Examples 3 and 4.

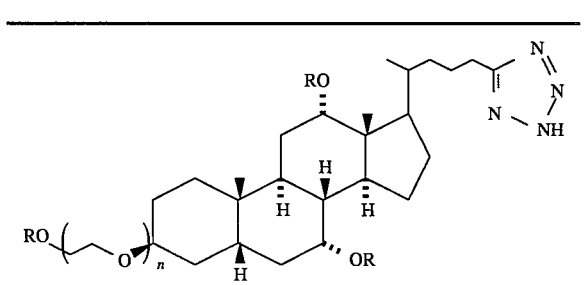

| Example | R | n | MS (FAB, 3-NBA/LiCl) |
|---|---|---|---|
| 13 | THP | 0 | C$_{40}$H$_{66}$N$_4$O$_6$ (698.5) 705.7 (M + Li$^+$) |
| 14 | H | 0 | C$_{25}$H$_{42}$N$_4$O$_3$ (446) 453 (M + Li$^+$) |
| 15 | THP | 1 | C$_{42}$H$_{70}$N$_4$O$_7$ (742.5) 749.4 (M + Li$^+$) |
| 16 | H | 1 | C$_{27}$H$_{46}$N$_4$O$_6$ (490) 497 (M + Li$^+$) |

EXAMPLE 17

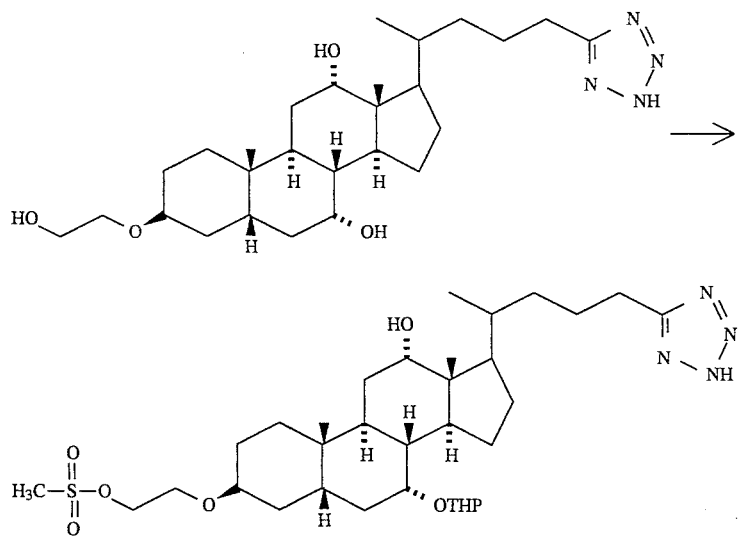

15 g (30.6 mmol) of the alcohol from Example 16 are dissolved in 200 ml of $CH_2Cl_2$, 100 ml of pyridine are added and the mixture is reacted with 5 ml of methanesulfonyl chloride at −20° to −10° C. for 2.5 hours. The still cold reaction solution is poured onto ice-water and extracted with ethyl acetate, and the organic phase is dried ($MgSO_4$) and concentrated. The crude product is purified over a short silica gel column ($CHCl_3/MeOH$ 93:7). 16 g (92%) of product are obtained.

MS (FAB, 3-NBA/LiCl) $C_{28}H_{48}N_4O_6S$ (568) 575 ($M+Li^+$)

EXAMPLE 18

C. for 2 hours. After cooling, the reaction mixture is concentrated and the residue is chromatographed over silica gel ($CH_2Cl_2/MeOH$ 85/15). The yield is 1.0 g (49%).

MS (FAB, 3-NBA/LiCl) $C_{27}H_{45}N_7O_3$ (515) 522 ($M+Li^+$)

EXAMPLE 19

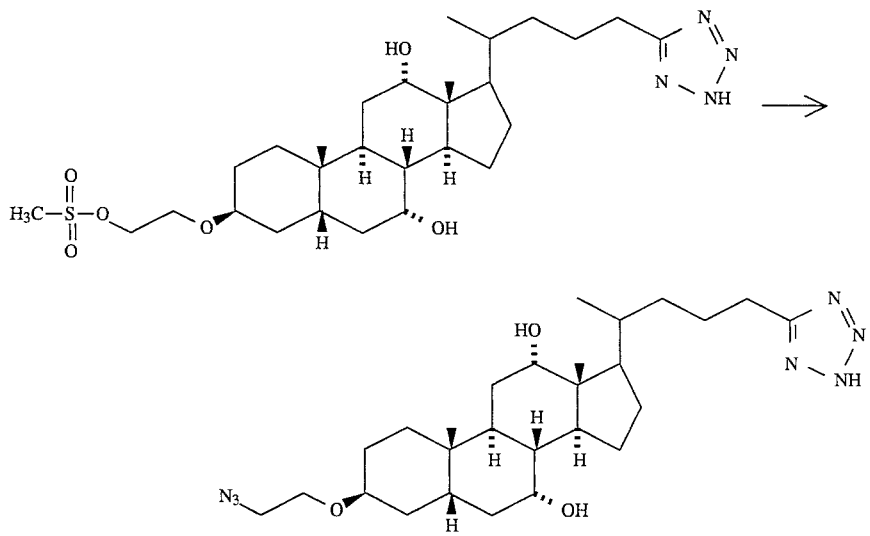

2.3 g (84.05 mmol) of mesyl compound (Example 17) and 290 mg of sodium azide are stirred in 30 ml of DMF at 100°

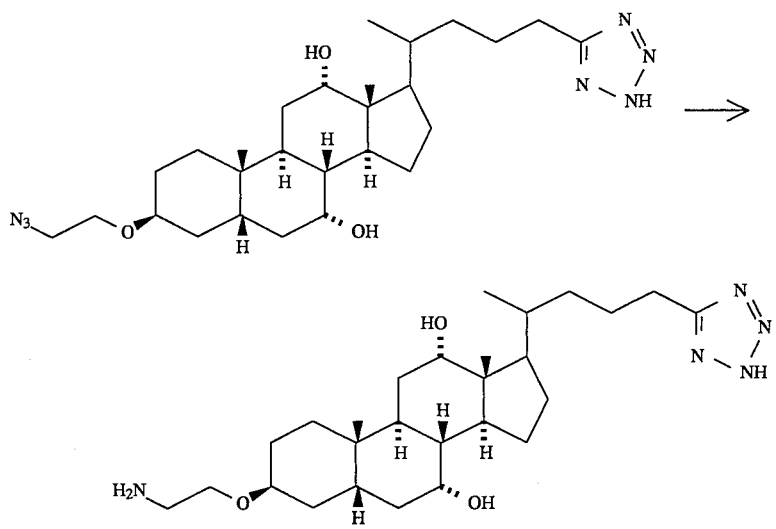

1.0 g (1.94 mmol) of azido compound are dissolved in 30 ml of methanol/1.5 ml of water and hydrogenated with $H_2$ in the presence of 50 mg of Pd black. The catalyst is filtered off and the filtrate is concentrated. The residue is chromatographed over silica gel ($CH_2Cl_2$/MeOH/$NEt_3$ 8:2:1), and 550 mg (58%) of amine are obtained.

MS (FAB, 3-NBA/LiCl) $C_{27}H_{47}N_5O_3$ (489) 496 (M+Li$^+$)

EXAMPLE 20

3.0 g (3.76 mmol) of the unprotected compound (EP-A-0 489 423) are dissolved in 30 ml of formic acid, 0.2 ml of perchloric acid is added and the mixture is stirred at 50° C. for 2 hours. 30 ml of acetic anhydride are then added dropwise at room temperature, and the mixture is stirred for a further 30 minutes. It is poured onto ice-water and extracted with ethyl acetate. The organic phase is dried and concentrated and the residue is chromatographed. 1.93 g (55%) of compound protected with formyl are obtained.

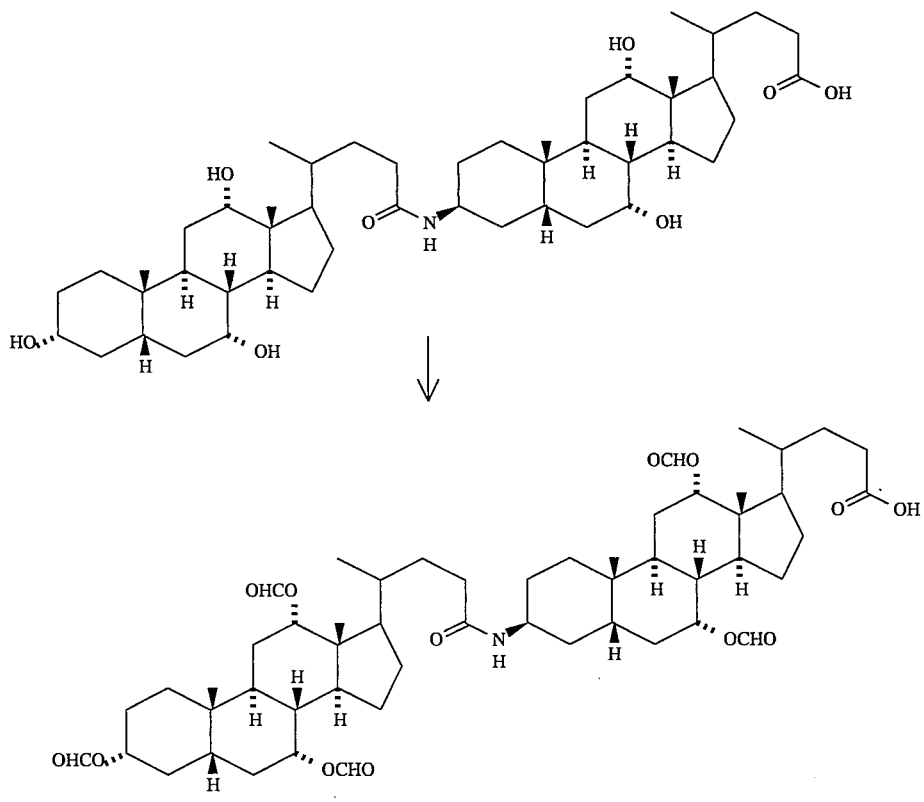

MS (FAB, 3-NBA) $C_{53}H_{79}NO_{13}$ (938) 939 (M+H$^+$)

EXAMPLE 21

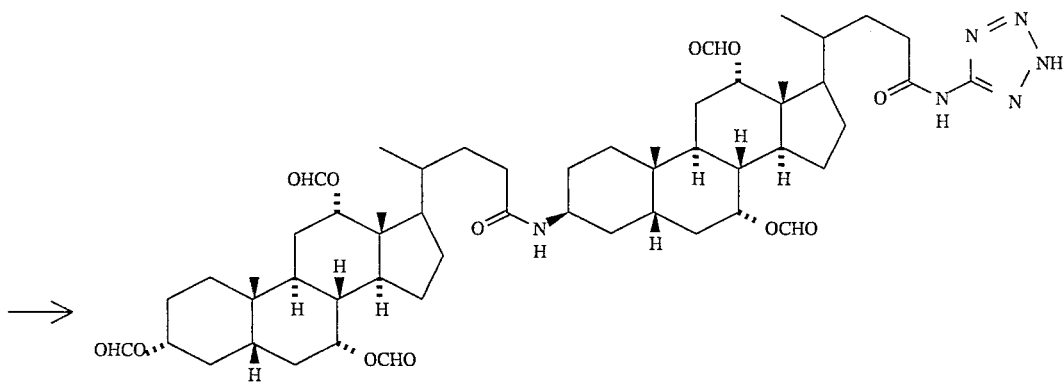

0.5 g (0.53 mmol) of Example 20 is dissolved in 30 ml of dry THF, 130 mg (0.62 mmol) of PCl$_5$ are added and the mixture is stirred at room temperature for 30 minutes. A solution of 200 mg (2.35 mmol) of anhydrous 5-aminotetrazole in 10 ml of DMF is added to the reaction solution. After a further 3 hours at room temperature, the mixture is concentrated and the residue is chromatographed (CHCl$_3$/MeOH 9:1). 400 mg (75%) of tetrazole compound are obtained.

MS (FAB, 3-NBA/LiCl) C$_{54}$H$_{80}$N$_6$O$_{12}$ (1005) 1012 (M+Li$^+$)

EXAMPLE 22

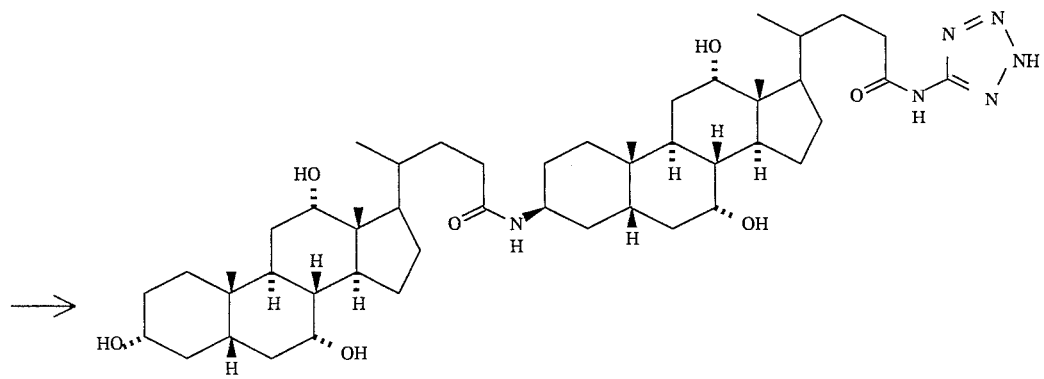

To split off the formyl groups, 370 mg (0.37 mmol) of Example 21 are dissolved in 20 ml of EtOH, 2 ml of 1N NaOH solution are added and the mixture is stirred at room temperature for 6 hours. It is then concentrated, water is added and 1N HCl is added to ~ pH 2. The precipitate is filtered off with suction and dissolved in methanol, the solution is filtered and the filtrate is concentrated again. 170 mg (53%) of product are obtained.

MS (FAB, 3-NBA/LiCl) C$_{49}$H$_{80}$N$_6$O$_7$ (865) 872 (M+Li$^+$)

Examples 23 and 24 are prepared from triformylcholic acid by the processes described for Examples 21 and 22.

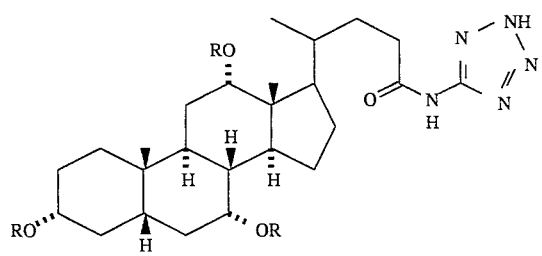

| Example | R | MS (FAB, 3-NBA/LiCl) |
|---|---|---|
| 23 | —CHO | C$_{28}$H$_{41}$N$_5$O$_7$ (559) 566 (M + Li$^+$) |
| 24 | H | C$_{25}$H$_{41}$N$_5$O$_4$ (475) 482 (M + Li$^+$) |

EXAMPLE 25

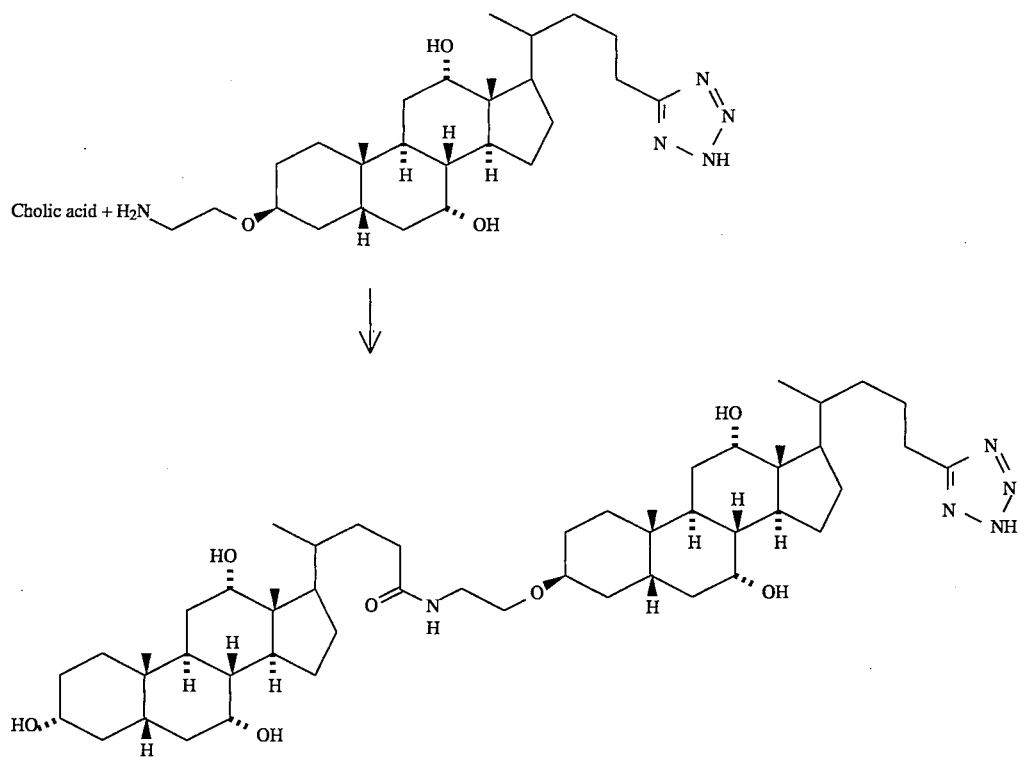

150 mg (0.31 mmol) of amino compound (Example 19), 130 mg (0.32 mmol) of cholic acid, 80 mg (0.64 mmol) of hydroxybenzotriazole and 65 mg (0.32 mmol) of dicyclohexylcarbodiimide are stirred in 20 ml of THF at room temperature for 24 hours. The reaction mixture is concentrated and the residue is chromatographed over silica gel ($CH_2Cl_2$/MeOH/$NEt_3$ 8:2:1). 250 mg (88%) of product are obtained.

MS (FAB, 3-NBA/LiCl) $C_{51}H_{85}N_5O_7$ (880) 887 (M+Li$^+$)

Examples 26 and 27 are obtained by the process described for Example 25.

| Example | R | MS (FAB, 3-NBA/LiCl) |
|---|---|---|
| 26 | α-OH | $C_{51}H_{85}N_5O_6$ (864) 865 (M + H$^+$) |
| 27 | β-OH | $C_{51}H_{85}N_5O_6$ (864) 865 (M + H$^+$) |

33
EXAMPLE 28

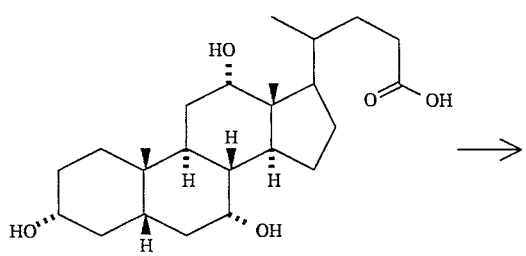

34
EXAMPLE 29

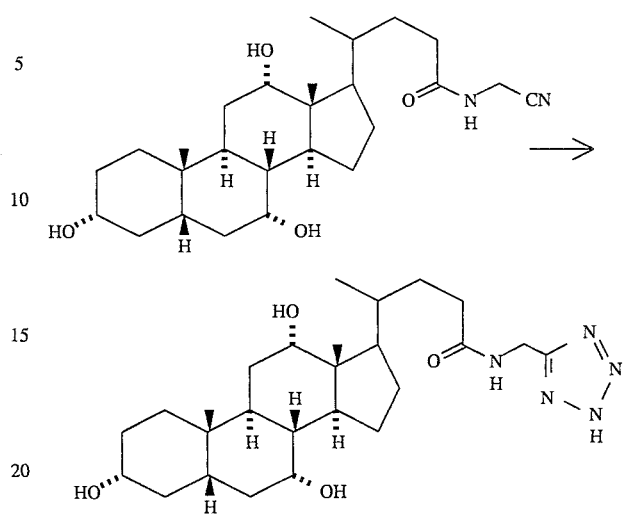

2.0 g (4.9 mmol) of cholic acid and 5 ml (36 mmol) of triethylamine are dissolved in 150 ml of THF, and 1.5 ml (16 mmol) of ethyl chloroformate are added at 0° C. After 15 minutes, 1.5 g (16 mmol) of aminoacetonitrile hydrochloride are added. The mixture is stirred at room temperature for 5 hours. The precipitate formed is filtered off and the solution is concentrated. After chromatography of the crude product (chloroform/methanol 17:3), 1.8 g of product (85%) are obtained.

MS (FAB, 3-NBA/LiCl) $C_{26}H_{42}N_2O_4$ (446) 453 (M+Li$^+$)

1.5 g (3.36 mmol) of the nitrile and 3.5 g (10.5 mmol) of tributyltin azide are heated under reflux in 100 ml of toluene for 24 hours. When the reaction has ended, the mixture is concentrated in vacuo and the residue is chromatographed over silica gel (CHCl$_3$/MeOH 7:3). 830 mg (56%) of product are obtained.

MS (FAB, 3-NBA) $C_{26}H_{43}N_5O_4$ (489) 490 (M+H$^+$)

Examples 30 and 31 were prepared by the processes described for Examples 28 and 29.

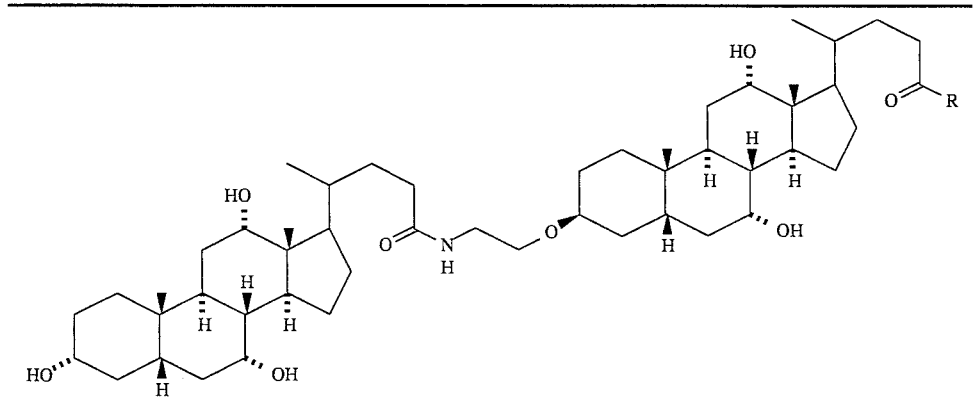

| Example | R | MS (FAB, 3-NBA/LiCl) |
|---|---|---|
| 30 |  | $C_{50}H_{81}N_3O_7$ (835.6) 842.6 (M + Li$^+$) |
| 31 |  | $C_{50}H_{82}N_6O_7$ (878.6) 891.7 (M + 2LiH$^+$) |

Table 1 shows measurement values for the inhibition of the [$^3$H]-taurocholate uptake in brush border membrane vesicles of the ileum from rabbits. The quotients of the IC$_{50}$ and IC$_{50Na}$ values of the reference substance taurochenodeoxycholate (TCDC) and the particular test substance are stated.

TABLE 1

| Compounds from Example | IC$_{50}$-TCDC [μmol] / IC$_{50}$-substance [μmol] | IC$_{50Na}$ TCDC [μmol] / IC$_{50Na}$-substance [μmol] |
|---|---|---|
| 4 | 0.28 | 0.38 |
| 14 | 1.20 | 1.35 |
| 16 | 0.26 | 0.25 |
| 22 | 1.66 | 1.35 |
| 24 | 0.97 | 1.27 |
| 27 | 0.26 | 0.25 |
| 29 | 0.46 | 0.48 |
| 31 | 1.39 | 1.24 |

We claim:

1. A tetrazole-bile acid derivative of the formula I

G1—X—G2 in which G1 is H or a radical of the formula II

[Structure of formula II: steroid ring system with R(1)O on ring A, R(2), R(3) on ring C, R(4), R(5) on ring B, and a side chain with CH$_3$ terminating in O=]

in which A and D indicate the ring structure according to IUPAC nomenclature rules, R(1) is H;
  an alkyl radical or alkenyl radical having up to 10 carbon atoms, which is branched or unbranched;
  a cycloalkyl radical having 3 to 8 carbon atoms;
  a benzyl radical which is unsubstituted or mono- to tri-substituted by F, Cl, Br, (C$_1$–C$_4$)-alkyl or (C$_1$–C$_4$)-alkoxy;
  a diphenylmethyl radical which is unsubstituted or mono- to tri-substituted by F, Cl, Br, (C$_1$–C$_2$)-alkyl or (C$_1$–C$_4$)-alkoxy;
  a triphenylmethyl radical which is unsubstituted or mono- to trisubstituted by F, Cl, Br, (C$_1$–C$_4$)-alkyl or (C$_1$–C$_4$)-alkoxy;
  a (C$_1$–C$_4$)-alkoxymethyl or a tetrahydroxylamyl radical; or
  a radical selected from the group consisting of $$O=\overset{\overset{OL}{|}}{\underset{\underset{OL}{|}}{P}}—, \quad O=\overset{\overset{OL}{|}}{\underset{\underset{O}{||}}{S}}— \quad \text{and} \quad L—\overset{\overset{O}{||}}{C}—$$

in which L is H;
  an alkyl or alkenyl radical having up to 10 carbon atoms, which is branched or unbranched;
  a cycloalkyl radical having 3 to 8 carbon atoms;
  a phenyl radical which is unsubstituted or mono- to trisubstituted by F, Cl, Br, (C$_1$–C$_4$)-alkyl or (C$_1$–C$_4$)-alkoxy; or
  a benzyl radical which is unsubstituted or mono- to trisubstituted by F, Cl, Br, (C$_1$–C$_4$)-alkyl or (C$_1$–C$_4$)-alkoxy;

X is a single bond or a bridge group of the formula III $$—[—(N)_s—A'—\underset{\underset{L(2)}{|}}{N}—\overset{\overset{O}{||}}{C}—(CH_2)_q—\overset{\overset{O}{||}}{C}—]_r—\underset{\underset{L(3)}{|}}{N}—(B)_t—$$
$$\phantom{—[—(N)_s}|$$
$$\phantom{—[—(N)_s}L(1)$$

in which
A' is a (C$_1$–C$_6$)-alkylene chain which is branched or unbranched and can optionally be interrupted 1 to 3 times by —O—, —S— or phenylene, the linkage to the phenylene ring being in the ortho-, meta- or para-position;
B is a (C$_1$–C$_6$)-alkylene chain, which is branched or unbranched and can optionally be interrupted 1 to 3 times by —O—, —S—, or phenylene, the linkage to the phenylene ring being in the ortho-, meta- or para-position;
L(1), L(2) and L(3) are identical or different and have the meaning of L;
q is 0 to 5;
r is 0 or 1;
s is 0 or 1;
t is 0 or 1;
R(2) and R(3) or R(4) and R(5) in each case together are the oxygen of a carbonyl group, or individually and in each case independently of one another are H, —OL, —SL, —NHL, tetrahydropyranyloxy or C$_1$–C$_4$-alkoxymethoxy, in which L has the abovementioned meaning; and G2 is a radical of the formula IV

[Structure of formula IV: steroid ring system with V—, W on ring A, R(6), R(7) on ring C, R(8), R(9) on ring B, and a side chain with CH$_3$ terminating in a tetrazole group Z—tetrazole—N.H$^\oplus$]

in which Z is $$—(CH_2)_m—\left(\overset{\overset{O}{||}}{C}—\underset{\underset{H}{|}}{N}\right)_n—(CH_2)_o—$$

where m is 0 to 4;
n is 0 or 1; and
o is 0 to 4;
V is attached to X and is selected from the group consisting of

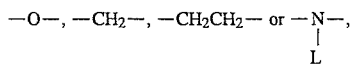

in which W is H; or if V is —CH$_2$— or —CH$_2$CH$_2$—, W is H or OH; and

R(6) to R(9) have the same meaning given for R(2) to R(5),

A and D indicate the ring structure according to the IUPAC nomenclature rules, and the linkage of G1 and G2 is via the ring D of G1 and the ring A of G2.

2. A compound of the formula I as claimed in claim 1, in which G1 is H or a radical of the formula II wherein R(1) is H, formyl, acetyl, benzoyl, methoxymethyl or tetrahydropyranyl;

R(2) and R(3) or R(4) and R(5) in each case together are the oxygen of a carbonyl group, or individually and independently of one another are H, OH, O-formyl, O-acetyl, O-benzoyl, methoxymethoxy or tetrahydropyranyloxy, X is a covalent bond or one of the following bridge groups

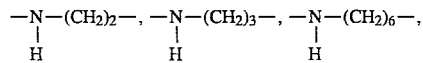

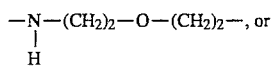

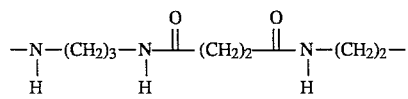

and G2 is a radical of the formula IV wherein

V is —O—, or

W is H; and

Z is

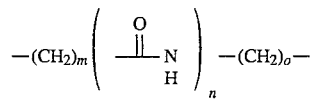

where m is 1 to 3;

n is 0 or 1;

o is 0, 1 or 2; and

R(6) to R(9) have the meaning given above for R(2) to R(5).

3. A method for lowering the lipid level of a host comprising administering an effective amount of a tetrazole-bile acid derivative of claim 1.

4. A medicament comprising a tetrazole-bile acid derivative as claimed in claim 1 and a pharmaceutically acceptable carrier.

5. A hypolipidemic composition comprising a tetrazole-bile acid derivative as claimed in claim 1 and a pharmaceutically acceptable carrier.

6. A method of using a tetrazole-bile acid derivative as claimed in claim 1 comprising administering an effective amount of a tetrazole-bile acid derivative as claimed in claim 1 to a host to lower the lipid level of said host.

7. A compound as claimed in claim 1 wherein in formula I, A is a C$_2$-C$_6$ chain.

8. A compound as claimed in claim 1 wherein in formula I, B is a C$_2$-C$_6$ chain.

* * * * *

UNITED STATES PATENT AND TRADEMARK OFFICE
CERTIFICATE OF CORRECTION

PATENT NO. : 5,466,815
DATED : November 14, 1995
INVENTOR(S) : Alfons ENHSEN et al.

It is certified that error appears in the above-indentified patent and that said Letters Patent is hereby corrected as shown below:

CLAIM 1, COLUMN 35, LINE 49, "$(C_1-C_2)$-alkyl" SHOULD READ --$(C_1-C_4)$-alkyl--.

Signed and Sealed this

Third Day of September, 1996

*Attest:*

BRUCE LEHMAN

*Attesting Officer*  *Commissioner of Patents and Trademarks*